United States Patent [19]

Meyer et al.

[11] Patent Number: 5,135,513

[45] Date of Patent: Aug. 4, 1992

[54] CONNECTOR FOR LIQUID TRANSFER DEVICE

[75] Inventors: Gabriel Meyer; Ernst Howald, both of Vesenaz, Switzerland

[73] Assignee: Medicorp Holding S.A., Luxembourg

[21] Appl. No.: 673,860

[22] PCT Filed: Dec. 21, 1987

[86] PCT No.: PCT/EP87/00812

§ 371 Date: Oct. 4, 1988

§ 102(e) Date: Oct. 4, 1988

[87] PCT Pub. No.: WO88/05668

PCT Pub. Date: Aug. 11, 1988

Related U.S. Application Data

[63] Continuation of Ser. No. 272,892, Oct. 4, 1988, abandoned.

[30] Foreign Application Priority Data

Feb. 5, 1987 [CH] Switzerland .................. 00413/87

[51] Int. Cl.[5] ............................................ A61M 5/00
[52] U.S. Cl. .................................. 604/240; 604/243; 604/411
[58] Field of Search ............... 604/168, 187, 207, 236, 604/238, 240, 243, 246, 283, 411, 414, 900; 222/564; 138/40, 44

[56] References Cited

U.S. PATENT DOCUMENTS

| | | | |
|---|---|---|---|
| 1,308,919 | 7/1919 | Sellar | 604/238 |
| 1,316,394 | 9/1919 | Sellar | 604/238 |
| 2,893,390 | 7/1959 | Lockhart | 604/238 |
| 3,030,953 | 4/1962 | Koehn | 604/168 |
| 3,352,306 | 11/1967 | Hirsch | 604/168 |
| 3,450,135 | 6/1969 | Sarnoff | 604/240 |
| 3,492,992 | 2/1970 | Kurtz | 604/168 |
| 3,886,930 | 6/1975 | Ryan | 604/236 |
| 4,193,400 | 3/1980 | Loveless et al. | 604/168 |
| 4,235,235 | 11/1980 | Bekkering | 604/238 |
| 4,269,186 | 5/1981 | Loveless et al. | 138/40 |
| 4,317,445 | 3/1982 | Robinson | 604/168 |
| 4,525,157 | 6/1985 | Vaillancourt | 604/168 |

FOREIGN PATENT DOCUMENTS 0154985  5/1952  Australia ...................... 604/240

*Primary Examiner*—John D. Yasko
*Assistant Examiner*—Anthony Gutowski
*Attorney, Agent, or Firm*—Davis, Bujold & Streck

[57] ABSTRACT

A transfer instrument (50), consisting of a prefilled disposable syringe, comprises a container (51) containing the liquid to be injected, a piston (52), and a piston rod (53) attached to the bottom of a capsule (54) with a tubular tip (58). This tubular tip has an inner surface (62) in the shape of a truncated cone to admit an insert (66) and an outer surface (64) in the shape of a truncated cone with a taper of 6%, capable of receiving a standard cap (59) fitted with a needle (60). A throat (73) is provided at the periphery of the insert (66) to permit the flow of the injection liquid and to obviate the need for a large dead volume.

19 Claims, 8 Drawing Sheets

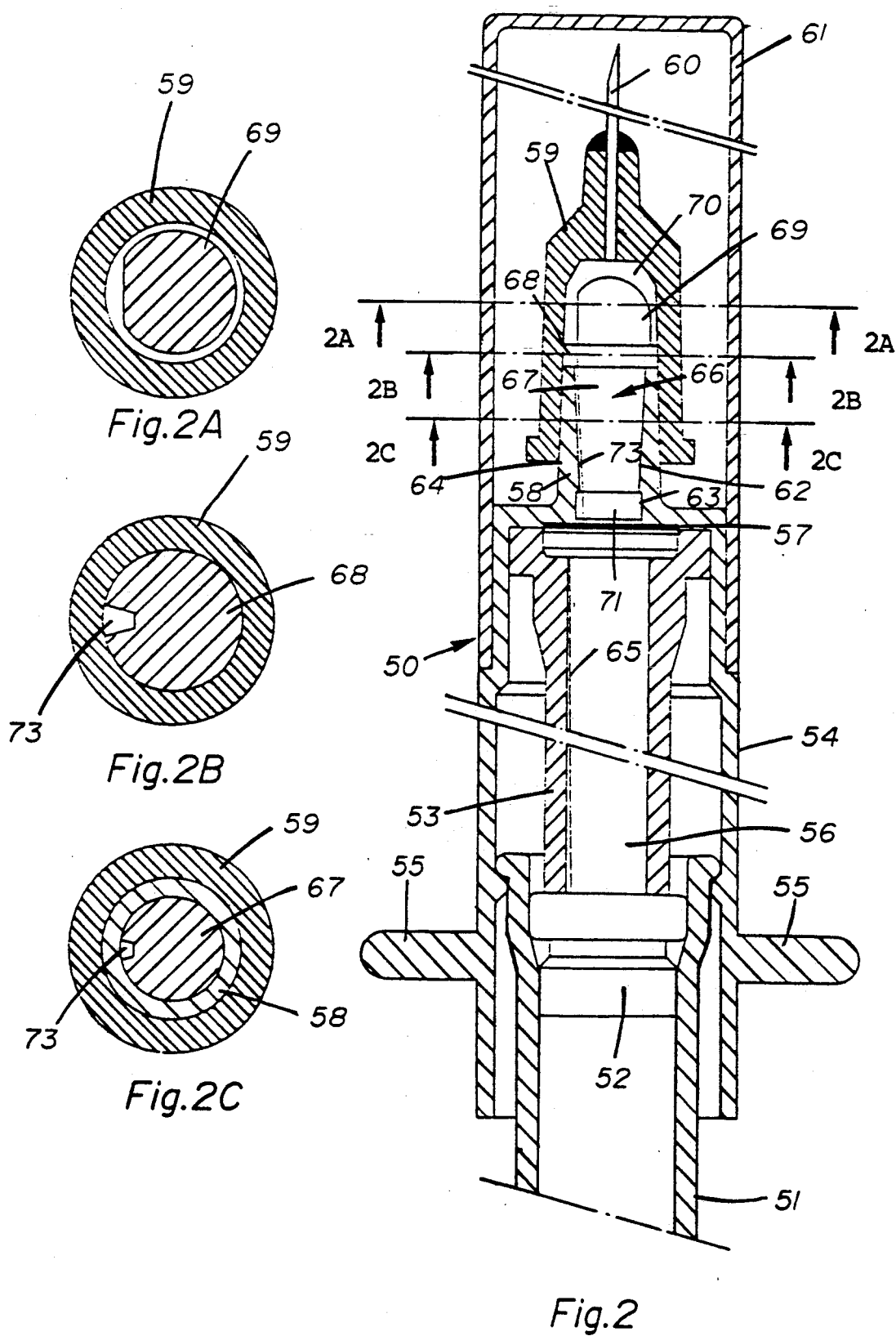

CONNECTOR FOR LIQUID TRANSFER DEVICE

This is a continuation of copending application Ser. No. 07/272,892 filed on Oct. 4, 1988, now abandoned.

BACKGROUND OF THE INVENTION

The present invention concerns a connector for adapting a tip to a liquid transfer device, particularly one for the transfer of liquid medicine.

Different means for connecting tips to liquid transfer devices are already known. One of these is described in U.S. Pat. No. 4,596,561, in which the transfer device is a prefilled single-dose hypodermic syringe and the tip is a needle connected to a cover adapted to a needle-holding ferrule disposed at the end of the syringe body.

One critical problem posed by these devices is that of unused contents, i.e., the quantity of medication remaining in the syringe after injection. The problem is particularly acute when the device is provided with a connector with a standard truncated Luer cone body of exterior dimensions approaching a 4 mm diameter and with a divergence of 6% along a length of from 7 to 10 mm. These exterior dimensions are necessary to allow the device to be attached to the standard female tips associated with such various elements as needles, multi-track valves, catheters, etc. In known manner, this standard truncated connecting device currently called the "conical Luer 6% connecting device" has a central conduit for the passage of liquid. Furthermore, it is known to be technically impossible to produce such a tip efficiently by means of thermoplastic injection molding when the central conduit has a relatively narrow ferrule, as the walls of the cone body then become proportionately too thick, thereby slowing down the injection cycle of the thermoplastic material considerably so that the cooling period for the material must be greatly increased to avoid shrinking.

To achieve a ferrule of the Luer type with a central canal diameter of the order of 0.4 mm, so as to result in relatively small amount of unused contents, the walls of the cone body should be a minimum of about 1.8 mm thick. This considerable thickness would require the synthetic material to undergo a lengthy cooling phase, during which bubbles would tend to form. Therefore, it would be nearly impossible to adhere to the parameters fixed by international norms for truncated male Luer 6%-type ferrules.

This is the reason that injection-manufactured disposable syringes presently in commerical use have a Luer ferrule axially transvesed by a central conduit with a diameter of the order of 3 mm, thereby permitting the walls to be thinner, of the order of 0.5 mm. This technological and economic imperative has the unfortunate result of leaving a larger quantity of unused contents inside the axial conduit of the ferrule.

This problem of unused contents has been approached and partially resolved by a device described in European Pat. Application published as No. 47042. The unused contents created by the relatively large dimensions of the axial conduit disposed inside the needle-holding ferrule of the syringe is partially overcome by insertion, during the final operation, of a truncated element connected to the piston extremity. However, this system does not resolve the problem of the standard unit described above, known as the Luer 6% truncated unit. In practice, when a truncated female element is adapted to a truncated male Luer 6% ferrule, a space always remains between the base of the female element and the extremity of the male ferrule, thereby affording little control over the amount of unused contents, a situaton which is both bothersome and dangerous, although useful in certain cases to serve as a viewing chamber for observing the passage of the liquid.

U.S. Pat. No. 4,240,425 proposes a unit which almost completely eliminates the problem of unused contents in injection syringes by providing on the one hand, a connecting device comprising a hollow tubular ferrule and on the other hand, a needle-bearing flange of essentially complementary shape adaptable to the said ferrule. The disadvantage of the this system resides in the fact that said needle-holding flange does not correspond to standard construction and therefore prevents replacement of the specialized needle by a standard needle if for some reason the special needle cannot be used. Actually, if a standard needle comprising a Luer 6% flange is placed in the ferrule of this syringe, the problem of unused contents described above surfaces again, and the patient is not injected with the prescribed dose of medication.

SUMMARY OF THE INVENTION

The present invention proposes to overcome all the foregoing disadvantages by realizing a connecting device of the type described, permitting use of tips with supports which conform to the norms imposed by the Luer 6%-type design principle, as well to resolve the problem of unused contents, particularly critical for injectable medication, especially with an extremely low volume of active substances.

To this end, the connecting device according to the invention is characterized by the fact that it comprises a tubular ferrule connected to the apparatus for liquid transfer, and an adapter connected to the tip, said ferrule having a central cavity and said adapter being associated with an insert disposed to engage within said central cavity, and by the fact that said insert comprises at least one longitudinal peripheral groove disposed to define, with the interior wall of the ferrule, a canal for the passage of the liquid to be transferred.

According to a first embodiment of the device, the insert and the adapter form a unit.

According to a second embodiment of the device, the insert is independent of the adapter.

The central cover of the tubluar ferrule preferably comprises a truncated interior wall whose generatrices converge towards the transfer apparatus.

The tubular ferrule preferably comprises an exterior truncated wall whose generatrices diverge towards the transfer apparatus. To enable use of a standard adapter conforming to the norms imposed by the Luer 6% design principle, the divergence of the truncated exterior wall of the tublar ferrule is preferably 6%.

According to a particulary advantageous embodiment of the connecting device, the tip is a trocar comprising a first portion with a truncated extremity, an intermediate portion and a second portion with a conical extremity, the said first portion of the extremity consisting of the said insert engaged in the central cavity of the tubular ferrule, the second intermediate portion having an exterior diameter greater than that of the wide end of the central cavity, and the three portions of said trocar being traversed by a longitudinal peripheral groove at least partially defining the canal for passage of the liquid to be transferred.

The intermediate portion of the trocar is disposed to contact the free extremity of the tubular ferrule.

According to another advantageous embodiment of the connecting device described, the tip is an injection needle, and the adapter comprises a bell-like cover disposed to adapt tightly over the tubular ferrule and holds the said injection needle. The insert, preferably independent of said cover, advantageously comprises a first truncated end portion engaged in the central cavity of the tubular ferrule, an intermediate portion and a second end portion engaged in the interior cavity of the said bell-shaped cover.

In this case, the shape of the second portion of the insert extremity is preferably designed so that it occupies only a portion of the free space within the interior cavity of the bell-shaped cover, so as to form a transparent control chamber for viewing the passage of the liquid through the cover wall.

Likewise, in this case, the intermediate portion of the insert is preferably disposed to contact the free end of the tubular ferrule and the interior wall of the said bell-shaped cover.

According to one preferred embodiment of the device, the tip is a nasal spray dispenser consisting of a rounded end portion formed at the extremity of an insert situated inside the tubular ferrule, and the canal for passage of the liquid to be transferred opens at the base of the rounded tip portion between the walls of the insert and those of the tubular ferrule. Said passageway preferably comprises a portion of the extremity forming an angle of from 30 to 90 degrees, and preferably approximately equal to 60 degrees, in relation to the tubular ferrule surface and/or to the insert in the area of the canal opening.

According to a first advantageous embodiment, the tip comprises a projected body within which there is mounted an insert defining, with the interior wall of said body, a passageway for the liquid, and said body comprises a stop means with a projection at a predetermined distance from the channel opening disposed to determine the depth for applying the liquid in the nasal cavities.

According to a second advantageous embodiment, the tip is a dropper, and the insert is provided with a flat element disposed at its upper extremity, said flat element comprising an opening extending the liquid passageway disposed between the said insert and the tubular ferrule. This tip is preferably surmounted by a cover consisting of a convex interior portion designed to let the cover open for passage of the gas inside the distributor and to seal it tightly. Said cover may comprise a base associated with an anti-bacterial agent.

BRIEF DESCRIPTION OF THE DRAWINGS

The present invention will be better understood with reference to the description of its embodiments and to the attached drawing in which;

FIG. 2 is a second embodiment of the apparatus according to the invention wherein the tip is an injection needle for liquid medication;

FIG. 2A is a transverse cross-section taken along line 2A—2A of FIG. 2;

FIG. 2B is a transverse cross-section taken along line 2B—2B of FIG. 2;

FIG. 2C is a transverse cross-section taken along line 2C—2C of FIG. 2;

DESCRIPTION OF THE PREFERRED EMBODIMENTS

Figures 1, 1A, 1B, 1C:
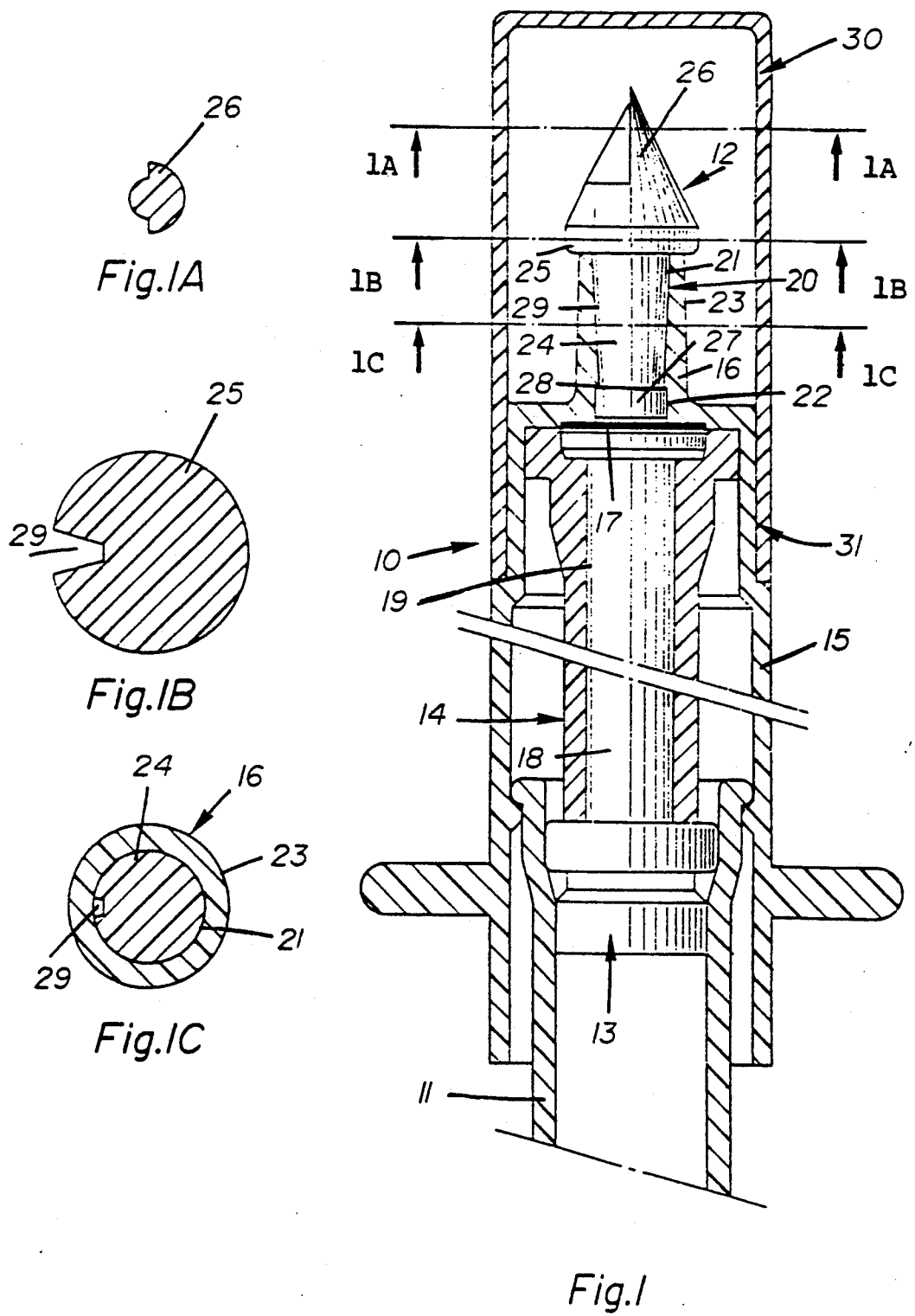
FIG. 1 shows a first embodiment of the device according to the invention wherein the tip is a trocar.
FIG. 1A is a tranverse cross-section taken along line 1A—1A of FIG. 1.
FIG. 1B is a transverse cross-section taken along line 1B—1B of FIG. 1
FIG. 1C is a transverse cross-section taken along line 1C—1C of FIG. 1.

FIG. 1 shows a device 10 for liquid transfer essentially comprising a receptacle 11 containing, for example, a liquid to be transferred into another receptacle holding a liquid or solid substance, such as, for example, a lyophilisate. Said other substance may be in a vessel or holder stoppered by a membrane to be pierced by a trocar 12 which comprises the tip associated with the transfer device. Said transfer device further comprises a piston 13 attached to the end of a shaft 14 attached, for example, by ultrasonic soldering or any other appropriate means, to the base of a capsule 15 having at its free end a tubular ferrule 16 with the said trocar 12 inside. A membrane filter 17 is mounted between the base of capsule 15 and shaft 14. The latter is hollow and has a pipe 18, generally cylindrical and equipped with an axial peripheral groove 19 forming with the interior wall of shaft 14 a longitudinal channel to allow liquid to flow through said shaft towards filter 17.

Tubular ferrule 16 (tubular end part) 16 comprises a central cavity 20 defined by a truncated interior wall 21 extending, at its end adjacent the base of capsule 15, into an annular cylindrical wall 22. Truncated wall 21 has generatrices which converge towards the transfer device. Exterior wall 23 of tubular ferrule 16 is also truncated, but its generatrices diverge towards the transfer device. Exterior wall 23 preferably has a 6% divergence to conform to international norms for Luer 6% design.

Trocar 12 comprises at least a first truncated portion 24 designed to be situated inside tubular ferrule 16. This portion comprises a lateral truncated surface with a conic section equal to that of interior wall 21 of tubular ferrule 16. It further comprises an intermediate portion 25, generally cylindrical, with a diameter greater than the interior diameter of the widest portion of the central cavity of tubular ferrule 16. While the diameter of intermediate portion 25 could be the same or smaller than the exterior diameter of tubular ferrule 16, the advantage of the larger diameter lies in reducing the risk of erroneously attaching a standard needle to a transfer device containing a substance requiring dilution before injection. Finally, trocar 12 comprises a third conical portion 26 designed to allow a membrane or cover to be pierced with a recipient for the liquid to be transferred, initially held in receptacle 11.

In the example shown, truncated portion 24 of the trocar extends into a cylindrical ring 27 defining an annular shoulder 28 with portion 24 to engage in the cylindrical opening defined by cylindrical wall 22 and disposed in the base of tubular ferrule 16 and across the base of capsule 15.

In this exemplary embodiment, the tip is a trocar, whose function has been described above. The adapter connected to the tip consists partly of the point or conical portion 26 of said trocar. The adapter is attached to the previously mentioned insert and these two elements are connected to form one element which is the truncated portion 24 of the trocar extending into cylindrical ring 27.

So that the liquid which has passed through filter 17 may flow towards the point of the trocar 12, cylindrical ring 27, truncated element 24, intermediate element 25 and conical element 26 of the trocar comprise a longitudinal peripheral groove 29 cooperating with walls 22 and 21 respectively disposed in the base of capsule 15 and inside tubular ferrule 16 to form a very narrow channel which allows liquid to flow but prevents formation of unused contents, which is very important for the transfer device concerned.

A protective cover 30 may be fitted over trocar 12 and attached by known means to capsule 15, which has an appropriate opening 31 in its base.

Cylindrical ring 27 comprises a retaining means cooperating with shoulder 28 to hold trocar 12 in place and to seal intermediate portion 25 tightly against the free end of tubular ferrule 16. Because of this, impermeability is perfectly assured at this level.

The same construction principle is used to create longitudinal conduit 19, thereby reducing the unused contents in the transfer device to an absolute minimum, that is, the volume of residual liquid after the transfer operation.

FIGS. 1A, B and 1C are a cross-section views showing the geometry of the different parts of the trocar taken along lines 1A—1A, 1B—1B and 1C—1C, respectively.

FIG. 2 shows a device for liquid transfer 50 in the form of a disposable single- or multiple-dose syringe. Said syringe essentially comprises a receptacle 51 for the injectable medication, a piston 52 engaged at the end of receptacle 51 and mounted on an essentially cylindrical shaft 53 attached, for example by ultrasonic soldering, to the base of capsule 54 comprising two flanges 55 for holding the syringe. Shaft 53 is hollow and has a generally cylindrical passageway 56. A filter 57 is located at the base of capsule 54. Said capsule extends into a tubular ferrule 58 consisting a needle-holding tip disposed to receive a bell-shaped cover 59 holding a needle 60. Before use, a protective cover is mounted on the end of capsule 54 to keep the needle in a sterile environment.

Tubular ferrule 58 has the same shape and dimensions as tubular ferrule 16 described with reference to FIG. 1. Its inside surface 62 is essentially truncated and extended by annular cylindrical wall 63 at its lower end. Its outside surface 64 is also truncated with a 6% divergence to allow attachment to a standard needle holder, so that it conforms to standard Luer 6%-type design. Cover 59 has a 6% interior divergence and adapts perfectly to tubular ferrule 58.

Passageway 56, located inside tubular shaft 53, prevents formation of too large a quantity of unused medication. The medication, which passes through piston 52 by means of a conduit (not shown), flows axially through a longitudinal channel defined by a groove disposed in the periphery of the tip of passageway 56 and by the interior wall of hollow cylindrical shaft 53. For the same reason, that is, to limit the amount of unused contents, i.e., the amount of medication remaining in the syringe after injection, an insert 66 is engaged within the truncated cavity defined by tubular ferrule 58. This insert essentially comprises a first truncated portion 67 completely engaged within tubular ferrule 58, an intermediate portion 68 in contact on the one hand with the annular surface of the end of tubular ferrule 58 and on the other hand with the interior wall of cover 59 holding needle 60, to form a sort of impermeable seal between these two components. The insert comprises a third portion 69 shared and dimensioned to only partially fill the remaining portion of the interior cavity of cover 59, so as to form a viewing chamber exposing the medication at the moment of injection through the transparent or semi-transparent wall of cover 59. The lower extremity of the first truncated portion 67 of insert 66 comprises a cylindrical element 71, the purpose of which is to form a retaining means to hold the insert in position within tubular ferrule 58. A groove 73 is disposed on the periphery of insert 66 to allow flow of the liquid which has passed through filter 57 and to lead into the viewing chamber communicating with the lower extremity of needle 60.

FIGS. 2A, 2B and 2C, which illustrate cross-sections taken along lines 2A—2A, 2B—2B and 2C-2C, respectively, show the shape of cover 59, of the upper portion 69 of insert 66, of the intermediate portion 68 of said insert, of the lower portion 67 of insert 66 and finally of passageway 73.

In this case, insert 66 is an independent piece forcibly engaged inside tubular ferrule 58 and designed to limit the amount of unused contents, that is, the residual amount of injectable medication after using the syringe, while permitting use of standard needles of Luer 6%-type design.

Figure 3:
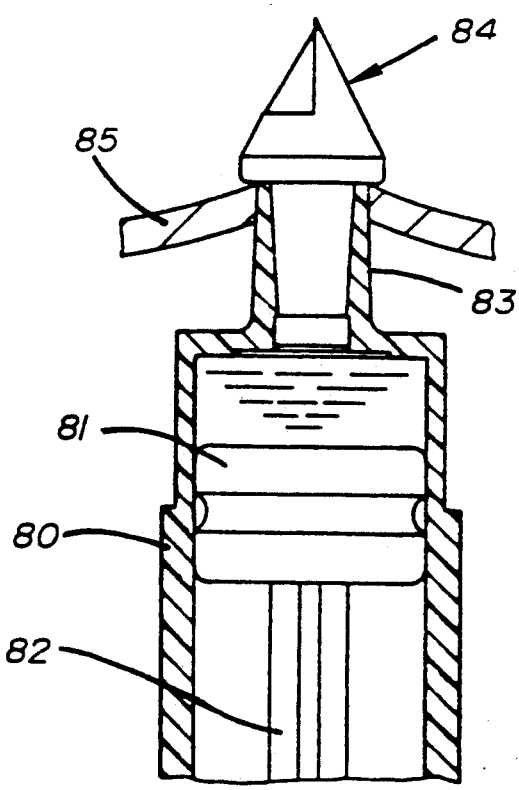
FIG. 3 is a variation of the device shown in FIG. 1.

FIG. 3 shows a variation of the device shown in FIG. 1. A conventional syringe 80 with a piston 81, affixed to an end of the shaft of piston 82, is provided with a tubular ferrule 83 identical to that describe with reference to FIG. 1. This ferrule receives trocar 84, identical in every respect to that described above. In this drawing, trocar 84 has been used to perforate membrane 85.

Figure 4:
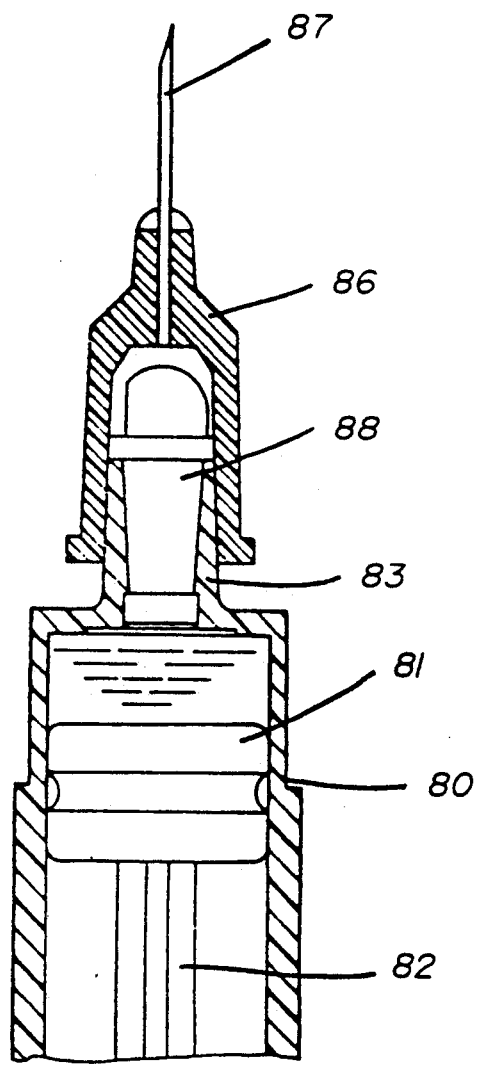
FIG. 4 is a variation of the device shown in FIG. 2.

FIG. 4 shows a syringe 80, identical to that of FIG. 3, comprising piston 81 affixed to the end of a shaft of piston 82 and provided with a tubular ferrule 83. A cover 86 holding needle 87 is attached to this ferrule, both identical in every respect to cap 59 and needle 60 shown in FIG. 2. An insert 88 is situated inside the ferrule of extremity 83. The devices of FIGS. 3 and 4 demonstrate that the truncated ferrule described above, capable of accommodating a standard Luer 6%-type design, may be adapted to any known transfer device.

Figure 5:
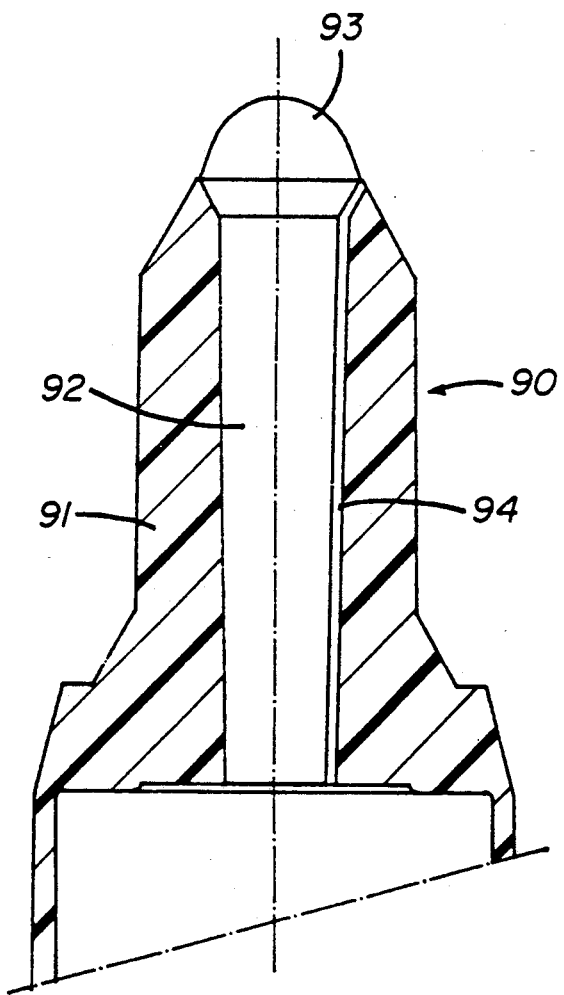
FIG. 5 is another connecting device according to the invention, which may be used as a nasal spray dispenser.

In the example of FIG. 5, the connecting device 90 is designed for use as a nasal spray, that is, to apply medication to the nasal membranes. As before, it comprises a tubular ferrule 91 with a central axial opening within which insert 92 is engaged. The central opening of tubular ferrule 91 is slightly conical. The lower portion of the insert to be engaged within the opening has the same shape. The upper extremity of insert 92 has an essentially spherical, rounded form to contact the membranes without risk of hurting them. A conduit 94 is disposed between the interior wall of tubular element 91 and the exterior wall of insert 92 to ensure the flow of liquid initially held in the recipient (not shown), to which the connecting device 90 is attached. This channel, essentially parallel to the axis of the lower portion of the insert, deviates and forms an angle of about 60 degrees in the area of its upper extremity. This inclination allows the medication to be applied directly to the mucous membranes and ensures ready absorption of the active product.

Figure 6:
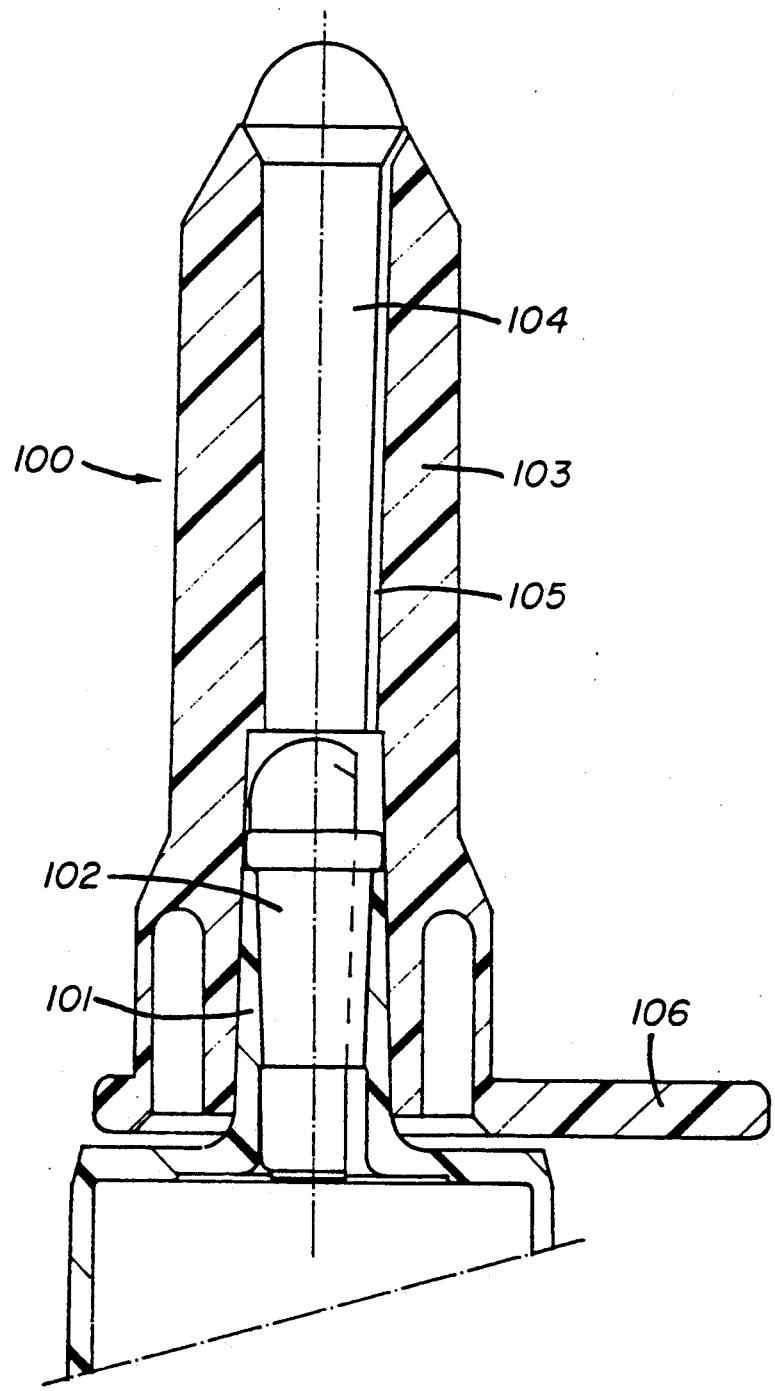
FIG. 6 is another variation of the connecting device according to the invention, which may also be used as a nasal spray.

FIG. 6 shows another embodiment of a nasal spray device which is in some respects a combination of the device shown in FIG. 2 with that of FIG. 5. Actually, this connecting device 100 comprises a tubular ferrule 101, inside of which there is an insert 102 essentially identical to insert 66 of the device of FIG. 2. The nasal spray device per se comprises a body 103 encasing tubular ferrule 101 which fits into insert 102. This tubular body comprises a central opening which is largely stoppered by a second insert 104, essentially identical to insert 92 shown in FIG. 5 and which has, between the inside wall of body 103 and the exterior wall of the said second insert 104, a lateral canal 105 essentially identical in shape and function to passageway 94 of the device of the preceding drawing. At its base, body 103 is provided with a flange 106 comprising a stop means whose function is to determine the depth at which the nasal spray is inserted into the nose, that is, the area where the medication will be applied. This depth is determined in such a way that the area for applying the medication corresponds to the optimal absorption area of the nasal mucous membranes.

Figure 7:
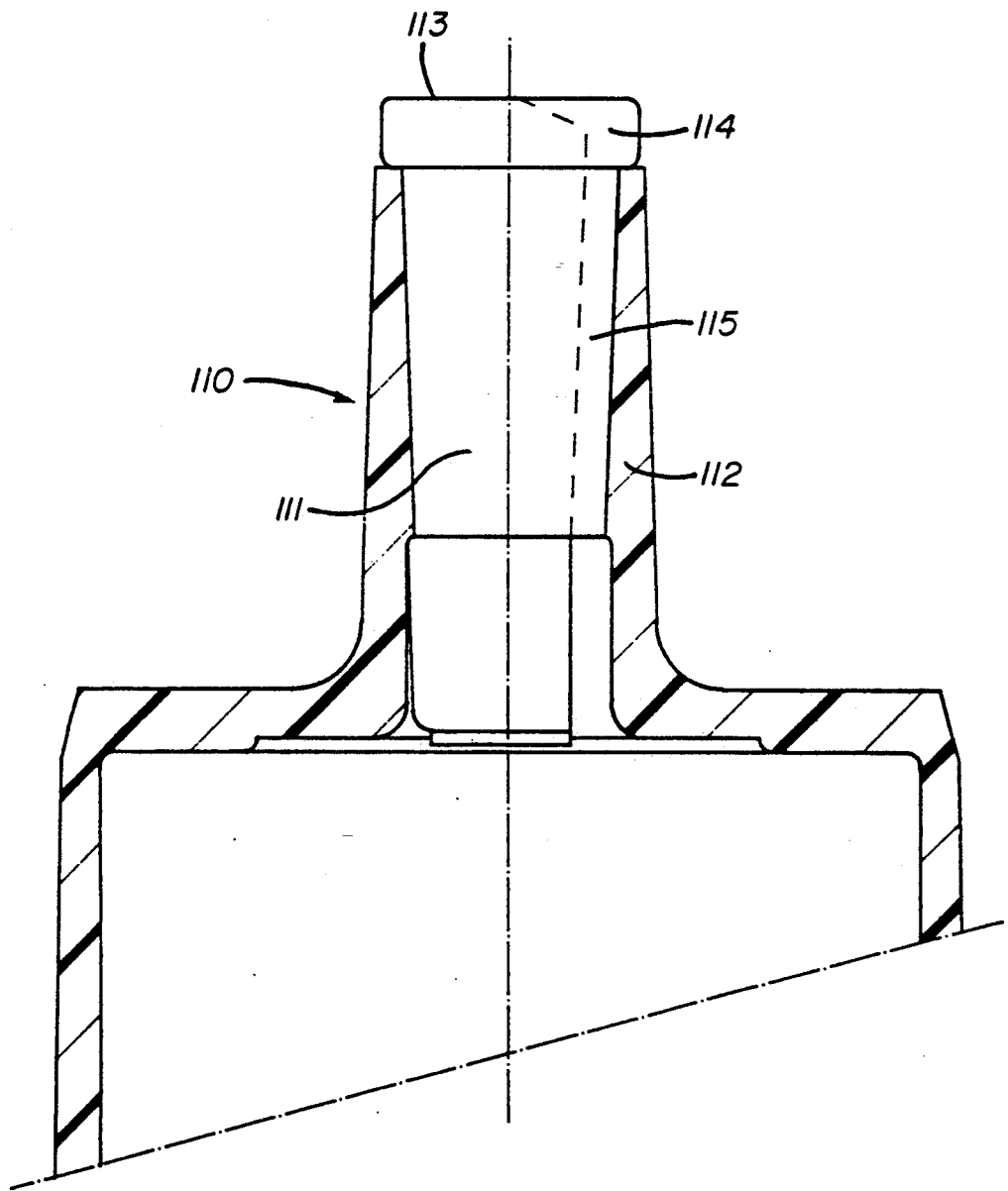
FIG. 7 is another embodiment of the connecting device according to the invention, which may be used as a dropper.

FIG. 7 shows another connecting device 110 used as a dropper. In this example, insert 111, situated inside of tubular ferrule 112, is surmounted by a flat element 113 provided with a peripheral notch 114 communicating with the longitudinal canal 115 defined by the interior wall of tubular ferrule 112 and by the wall of an axial notch disposed in insert 111.

Figure 8:
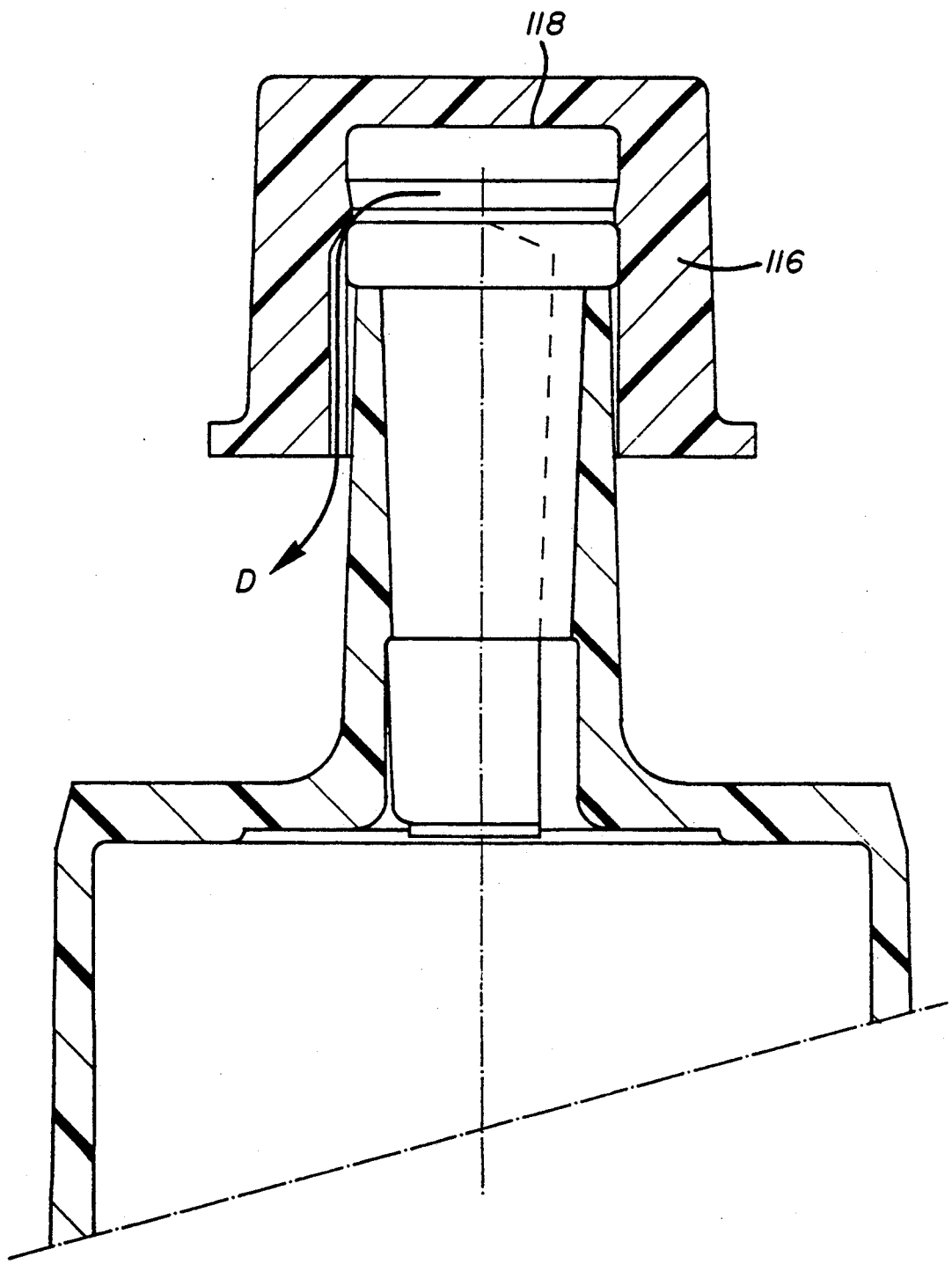
FIGS. 8 and 9 show a cover for closing the dropper of FIG. 7, in the open and closed positions, respectively.
Figure 9:
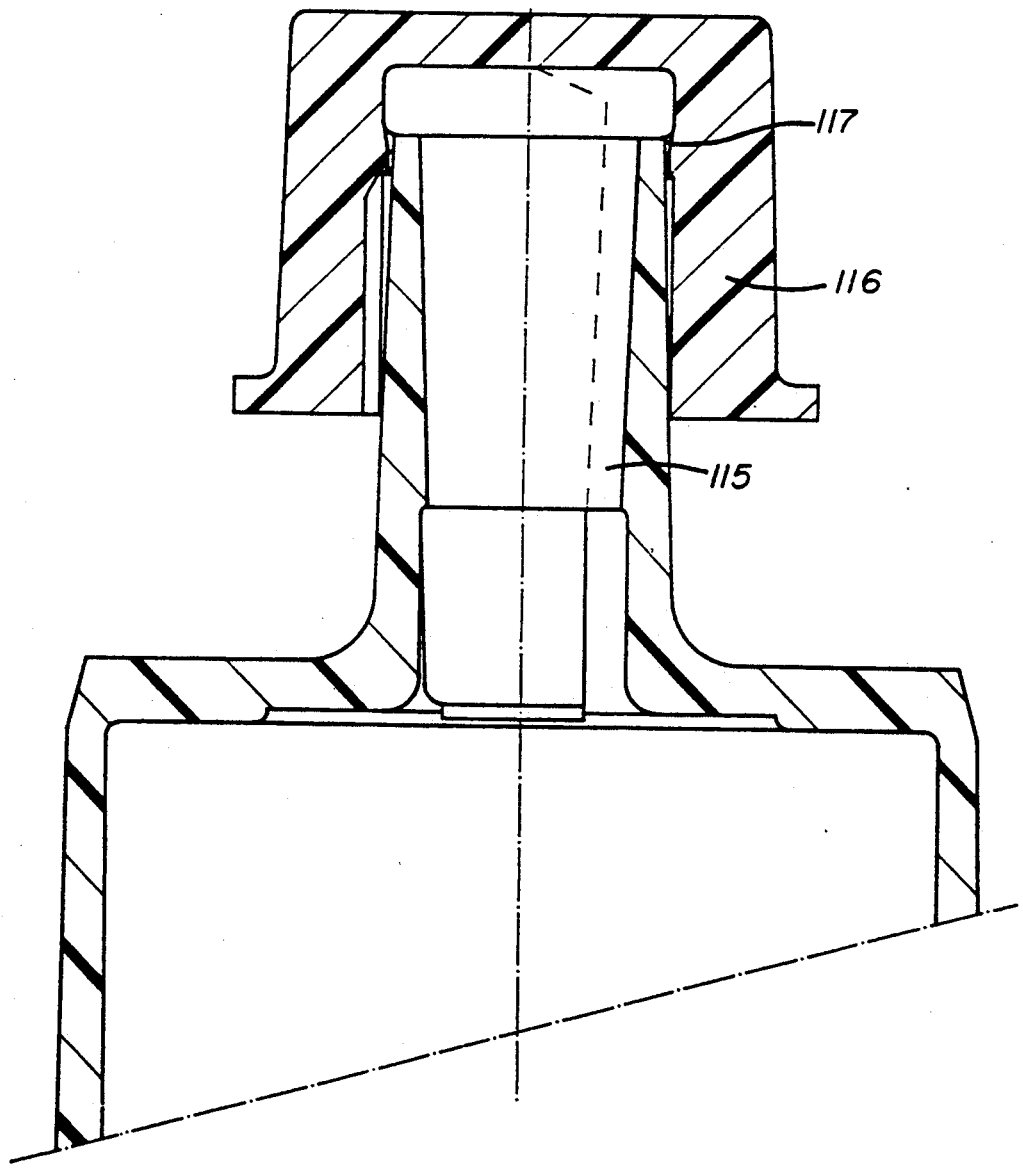

FIGS. 8 and 9 expand upon the device shown in FIG. 7 with the addition of a tightly sealing cover 116. In FIG. 8, the cover 116 is in the open position for decompression, i.e., evacuation of the air inside the distributor body in the direction of arrow D. In FIG. 9, cover 116 is shown in the closed position to ensure tight sealing of distributor channel 115. To achieve this, the interior lateral wall of cover 116 comprises an annular protrusion 117 which, because of the relative elasticity of the material, can be moved over flat element 114 surmounting insert 11 to contact the exterior wall of tubular ferrule 112 beneath said flat area. The base 118 of the interior cavity or cap 116 may be treated with an anti-bacterial agent, or may contain a small anti-bacterial plate to permanently disinfect the area where the liquid flows through the dropper. This arrangement is particualrly advantageous in a dropper system designed for numerous uses, where each use places the dropper in contact with the environment and contaminates it. Between uses, the storage period activates the anti-bacterial substance and thus systematically decontaminates the contaminated portion.

It is understood that the present invention is not limited to the embodiments described, but may be modified and undergo various changes obvious to one skilled in the art. Thus, the shape and dimensions of the various components of the droppers or nasal spray applicators, as well as of the protective cover and finally the anti-bacterial agent, may be modified according to need or requirements imposed by either use or manufacture.

In the case of the nasal spray, the parameters, the stop means, the slope of the channel extremity and its diameter may be modified according to the type of medication to be administered and its viscosity. The position of the flange of the stop means shown in FIG. 6 further depends upon the location of the optimal absorption area in the nasal mucous membranes. In the case of the dropper, the exterior shape of the insert may be adapted to the desired use for the dropper. The intention is to apply a calibrated drop in the eyes, on the body surface, in the mouth or even into a receptacle for dilution with water or other liquid for absorption. The fundamental advantage of such a dropper, mounted on a piston distributor, is that the evacuation of the drop is controlled by piston action. Unlike conventional droppers, there is no reabsorption of gas inside the distributor body and therefore no risk of contaminating the medicated solution inside the distributor.

We claim:

1. A transfer device for transferring a liquid medication from a first receptacle to one of a second receptacle or for injecting the same into patient, the transferring device comprising:

a rigid body having a first end thereof with means for engaging and securing the body to the first receptacle, and a second end thereof, opposite the first end, having a tubular end part defining an inner cavity, the body having means for allowing flow of the liquid medication from the first end to the tubular end part;

a tip attached to the tubular end part for facilitating the transfer of the liquid medication from the tubular end part to one of the second receptacle or the patient; and an insert member having at least a portion of its exterior surface closely conforming to the shape and size of the cavity of the tubular end part and the insert member being at least partially insertable within the cavity;

wherein at least one of the exterior surface of the insert member or the interior surface of the tubular end part is provided with a longitudinal peripheral groove forming a longitudinal passageway, between the interior and exterior surfaces within the tubular end part when the insert member is inserted within the cavity and the tip is attached to the tubular end part, extending between the means for allowing flow and the tip to allow the flow of the liquid medication therebetween, and means for fixedly locating axially the insert member relative to the cavity of the tubular end part.

2. A device according to claim 1, wherein an adapter is provided for connecting the tip to the tubular end part.

3. A device according to claim 2, wherein the insert member and the adapter are integrally formed.

4. A device according to claim 2, wherein the insert member and the adapter are separate elements.

5. A device according to claim 1, wherein the means for fixedly locating axially the insert member comprises the cavity of the tubular end part having a truncated interior surface, which converges towards the first end of the transfer device, mating with a corresponding diverging exterior surface of the insert member.

6. A device according to claim 1, wherein the tubular end part comprises a truncated exterior surface which diverges toward the first end of the body.

7. A device according to claim 6, wherein the exterior wall of the tubular end part has a 6% divergence.

8. A transfer device for transferring a liquid medication from a first receptacle to one of a second receptacle or for injecting the same into a patient, the transferring device comprising:

a body having a first end thereof with means for engaging and securing the body to the first receptacle, and a second end thereof, opposite the first end, having a tubular end part defining an inner cavity, the body having means for allowing flow of the liquid medication from the first end to the tubular end part;

a tip attached to the tubular end part for facilitating the transfer of the liquid medication from the tubular end part to one of the second receptacle or the patient;

an insert member having at least a portion of its exterior surface closely conforming to the shape and size of the cavity of the tubular end part and the insert member being at least partially insertable within the cavity;

wherein at least one of the exterior surface of the insert member or the interior surface of the tubular end part is provided with a longitudinal peripheral groove forming a passageway within the tubular end part, when the insert member is inserted within the cavity and the tip is attached to the tubular end part, between the means for allowing flow and the tip to allow the flow of the liquid medication therebetween;

an adapter connects the tip to the tubular end part;

the tip is an injection needle and the adapter is a bell-shaped cover disposed to fit tightly over an exterior surface of the tubular end part and hold the injection needle, and the insert member is independent of the bell-shaped cover and comprises a first end portion engaged within the cavity of the tubular end part, an intermediate portion, and a second end portion engaged within an interior cavity of the bell-shaped cover.

9. A device according to claim 8, wherein the bell-shaped cover includes a transparent wall and the second end portion of the insert member occupies only a portion of the interior cavity of the bell-shaped cover so as to form a control chamber for viewing, via the transparent wall, passage of the medication through the bell-shaped cover.

10. A device according to claim 8, wherein the intermediate portion of the insert member is disposed in contact with the tubular end part and with the interior wall of the bell-shaped cover.

11. A transfer device according to claim 1, wherein the tip is a trocar having three sequentially arranged portions comprising a first truncated end portion forming the insert member, an intermediate portion and a conical end portion, at least a portion of the intermediate portion has a larger exterior diameter than the insert member, and the three sequentially arranged portions of the trocar are traversed by a peripheral longitudinal opening at least partially defining the passageway for passage of the liquid medication to be transferred.

12. A transfer device according to claim 11, wherein the intermediate portion of the trocar is disposed to contact a free end of the tubular end part remote from the first receptacle.

13. A transfer device according to claim 1, wherein the tip is a nasal spray applicator comprising a rounded end portion formed in an end of the insert member remote from the first receptacle, and an outlet of the passageway for the liquid medication to be transferred is provided in a base of the rounded end portion between an exterior surface of the insert member and an interior surface of the tubular end part.

14. A transfer device according to claim 13, wherein the outlet extends at an angle of from 30 to 90 degrees in relation to a central axis of the tubular end part.

15. A transfer device according to claim 13, wherein the tip comprises a projecting body which has, mounted therein, a second insert member having an exterior surface defining with an interior surface of the projecting body a further passageway for the transfer of liquid medication from the transfer device, and the projecting body including exterior stop means, located at a predetermined distance from an outlet of the further passageway, for limiting insertion of the projecting body inside a nostril of the patient.

16. A transfer device according to claim 1, wherein the tip is a dropper and the insert member is provided with a flat element at an end thereof remote from the first receptacle, and the flat element comprising an outlet communicating with the passageway for dispensing the liquid medication from the transfer device.

17. A transfer device according to claim 1, wherein the tip is surmounted by a cover having an annular interior ring disposed therein to ensure that the cover, when in a first position, allows a gas inside the transfer device to flow out through the outlet and, when in a second position, tightly closes the outlet.

18. A transfer device according to claim 17, wherein the cover comprises an interior base portion which is treated with an anti-bacterial agent.

19. A transfer device for transferring a liquid medication from a first receptacle to one of a second receptacle or for injecting the same into a patient, the transferring device comprising:

a rigid body having a first end thereof with means for engaging and securing the body to the first receptacle, and a second end thereof, opposite the first end, having a tubular end part defining an inner cavity, the body having means for allowing flow of the liquid medication from the first end to the tubular end part;

a tip attached to the tubular end part for facilitating the transfer of the liquid medication from the tubular end part to one of the second receptacle or the patient; and an insert member having at least a portion of its exterior surface closely conforming to the shape and size of the cavity of the tubular end part and the insert member being at least partially insertable within the cavity;

wherein at least one of the exterior surface of the insert member or the interior surface of the tubular end part is provided with a longitudinal peripheral groove forming a longitudinal passageway within the tubular end part, when the insert member is inserted within the cavity and the tip is attached to the tubular end part, between the means for allowing flow and the tip to allow the flow of the liquid medication therebetween, the longitudinal passageway is defined by and extends longitudinally between the exterior surface of the insert member and the interior surface of the tubular end part, and means for locating axially the insert member at a fixed position relative to the cavity of the tubular end part.

* * * * *